United States Patent [19]

Rosenson

[11] Patent Number: 4,720,462

[45] Date of Patent: Jan. 19, 1988

[54] CULTURE SYSTEM FOR THE CULTURE OF SOLID TISSUE MASSES AND METHOD OF USING THE SAME

[76] Inventor: Robert Rosenson, 6408 Irwin Ct #1, Oakland, Calif. 94609

[21] Appl. No.: 794,968

[22] Filed: Nov. 5, 1985

[51] Int. Cl.$^4$ ............................................. C12M 3/04
[52] U.S. Cl. ................................. 435/285; 435/240.1; 435/289; 435/313
[58] Field of Search ............................... 435/284–287, 435/289, 313, 240, 241; 210/321.4, 221.2; 261/122

[56] References Cited

U.S. PATENT DOCUMENTS

| | | | |
|---|---|---|---|
| 3,768,977 | 10/1973 | Brumfield et al. | 23/258.5 |
| 3,883,393 | 5/1975 | Knazek et al. | 435/285 |
| 3,985,622 | 10/1976 | Hawkins | 435/289 |
| 3,997,396 | 12/1976 | Delenie | 435/240 |
| 4,051,025 | 9/1977 | ito | 210/635 |
| 4,087,327 | 5/1978 | Feder et al. | 435/240 |
| 4,184,922 | 1/1980 | Knazek et al. | 435/284 |
| 4,201,845 | 5/1980 | Feder et al. | 435/316 |
| 4,220,725 | 9/1980 | Knazek et al. | 435/285 |
| 4,378,434 | 3/1983 | Prentice et al. | 435/157 |
| 4,379,846 | 4/1983 | Shkidchenko et al. | 435/316 |
| 4,391,912 | 7/1983 | Yoshida et al. | 435/241 |
| 4,440,853 | 4/1984 | Michaels et al. | 435/68 |
| 4,444,882 | 4/1984 | Shimizu et al. | 435/29 |
| 4,537,860 | 8/1985 | Tolbert et al. | 435/240 |

OTHER PUBLICATIONS

Blanch et al., "Rapid Production of Biological Products by Fermentation in a Densely Packed Microbiol Membrane Reactor", 5/24/84, PCT I.P.N. WO84/01959.
K. Ku et al.; "Development of a Hollow-Fiber System for Large-Scale Culture of Mammalian Cells"; *Biotechnology and Bioengineering*, vol. XXIII, pp. 79–95, (1981).
Douglas S. Inloes, et al.; "Hollow-Fiber Membrane Bioreactors Using Immobilized *E. coli* for Protein Synthesis"; *Technology and Bioengineering*, vol. XXV, pp. 2653–2681, (1983).
W. David Deeslie, et al.; "A CSTR-Hollow-Fiber System for Continuous Hydrolysis of Proteins."; *Biotechnology and Bioengineering*, vol. XXIV, pp. 69–82, (1982).

(List continued on next page.)

Primary Examiner—James C. Young
Assistant Examiner—Noah P. Kamen
Attorney, Agent, or Firm—Browdy and Neimark

[57] ABSTRACT

A culture tube is divided into 5 sealed chambers: a gaseous supply chamber; a liquid supply chamber; a culture chamber; a gaseous return chamber and a liquid return chamber. Cell-impermeable hydrophilic tubes extend from the liquid supply chamber, through the culture chamber to the liquid return chamber. Liquid nutrient flows in the tubes and perfuses through the walls thereof under differential pressure to nourish the cells in the culture chamber. Cell-impermeable hydrophobic tubes extend from the gaseous supply chamber, through the culture chamber, to the gaseous return chamber to provide respiratory gases to and remove waste gases from cells in the culture chamber. The apparatus is designed to be a radially symmetric and thus, provide a uniform tissue culture. Pressure indicators flush-mounted on the walls of the chamber tube, may be provided to monitor chamber conditions and relay this information to a micro-computer which enriches the culture chamber environment. A central tube extends along the longitudinal axis of the culture tube, and is appropriately sectioned and modified to supply liquid nutrient to the liquid supply chamber and remove waste fluids including soluble product, from the culture chamber. In another embodiment, a single cell impermeable, hydrophilic tube extends through the culture apparatus and the filtrate is still removed by the central macroporous tubes. In this embodiment, there is no need for a liquid return chamber.

18 Claims, 19 Drawing Figures

OTHER PUBLICATIONS

A. Prokop, et al.; "Hydrodynamics, Mass Transfer, and Yeast Culture Performance of a Column Bioreactor with Ejector"; *Biotechnology and Bioengineering*, vol. XXV, pp. 1147–1169, (1983).

Mauro Moresi, et al.; "The Ejector–Loop Fermenter: Description and Performance of the Apparatus"; *Biotechnology and Bioengineering*, vol. XXV, pp. 2889–2904, (1983).

Paul Van Hemert; "The "Bilthoven Unit" for Submerged Cultivation of Microorganisms", *Biotechnology and Bioengineering*, vol. VI, pp. 381–401, (1964).

Joseph Feder et al.; "The Large—Scale Cultivation of Mammalian Cells"; from *Scientific American*, Jan. 1983, vol. 248, No. 1.

M. W. Glacken, et al.; "Large-Scale Production of Mammalian Cells and Their Products": Engineering Principles and Barriers of Scale–Up"; *Annals New York Academy of Sciences*.

Ciftci, et al.; "Annals New York Academy of Sciences".

Jay M. S. Henis, et al.; "The Developing Technology of Gas Separating Membranes"; *Science;* 1 Apr. 1983, vol. 220, No. 4592.

From Perry's "Handbook for Chemical Engineers"; Title: Fluid Distribution.

Kirk-Othmer; "Encyclopedia of Chemical Technology"; Title: Matches to N-Nitrosamines; vol. 15, (1981).

"System Measures Cells' Activity Level"; from *Chemical Engineering*, Apr. 2, 1984–New Products & Services.

R. D. Walker, et al.; "A System for Automation of Tissue Culture"; Reprinted from *American Biotechnology Laboratory*, Dec. 1983.

"Automated Perifusion Culture Systems", from *Acusyst*.

Jeffrey Ringhofer; "Mammalian Cell Scale-Up Technologies"; *Production of Mammalian Cell Products: A Marketing Focus*.

"Acusyst-P Production System for Mammalian Cell Products".

"Series of Automated Culture Systems"; From *Acusyst*.

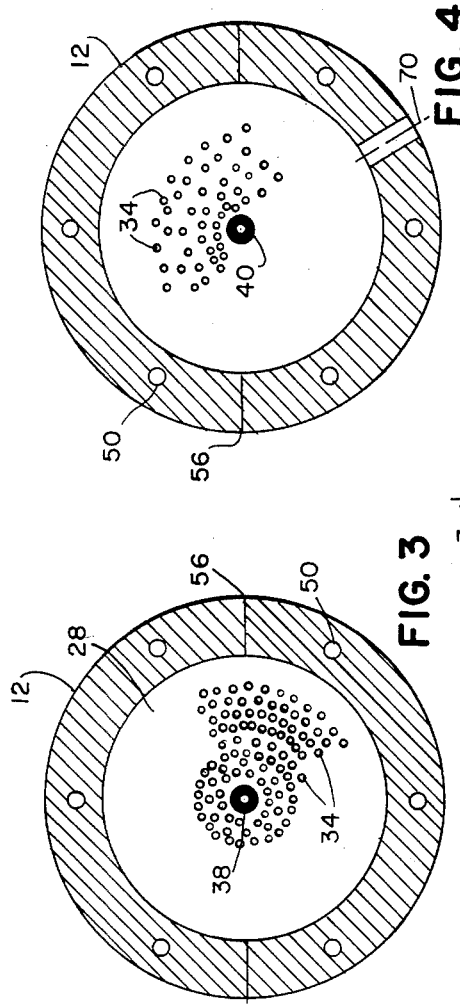
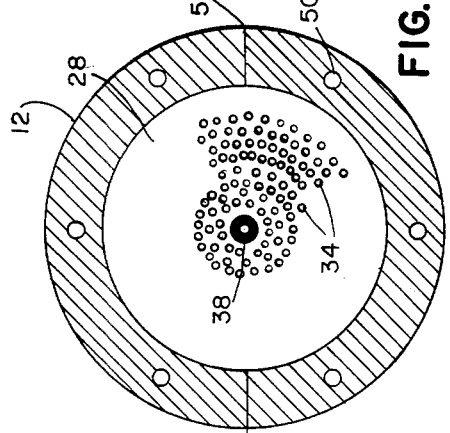
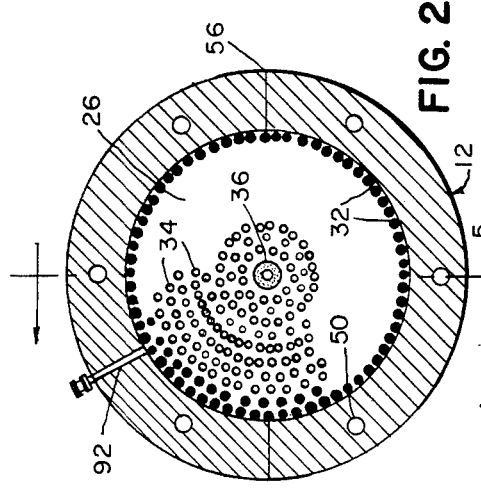
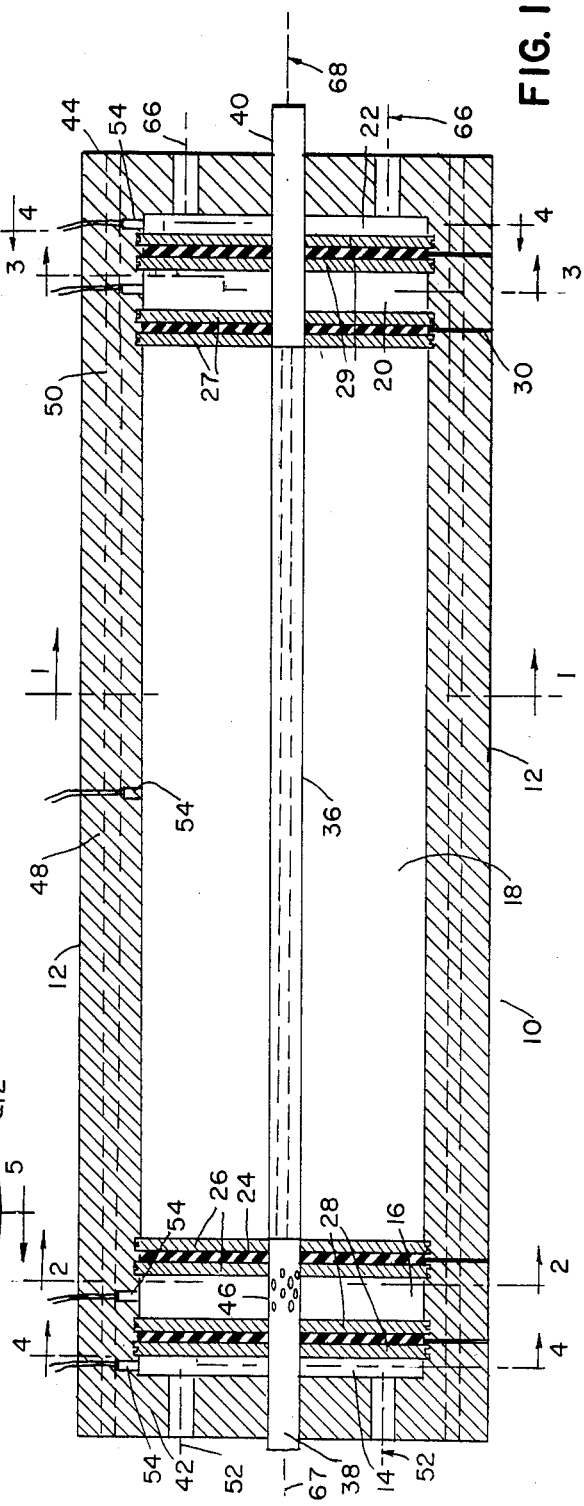

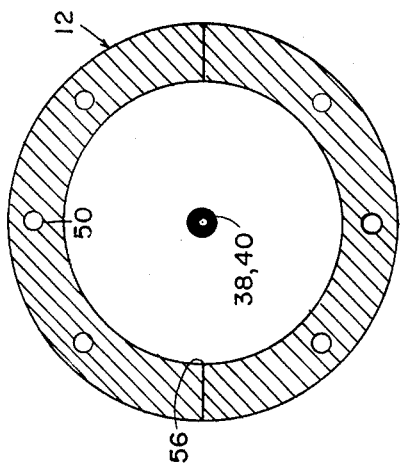

CULTURE SYSTEM FOR THE CULTURE OF SOLID TISSUE MASSES AND METHOD OF USING THE SAME

FIELD OF THE INVENTION

This invention relates generally to cell culture systems and more particularly to cell culture systems for solid tissue cultures.

BACKGROUND OF THE INVENTION

Tissue cultures are used for many purposes and especially for the production of therapeutic proteins and polypeptides. Preferably, a tissue culture should define a dense mass which is uniform or at least as symmetric as possible. Thus, tissue culture systems should preferably assure that all cells receive adequate nutrition and oxygen for proper growth and each cell should receive about the same amount of oxygen and nutrient, or at least each cell of a geometrically symmetrically located pair should receive about the same amounts of oxygen and nutrients. Otherwise, some tissue necrosis will occur.

To date various systems have been used for the culture of mammalian cells. These systems have employed sponge matrices, multiple tubing, stacked-plate systems, coiled plastic films or micro-carrier suspension cultures. A device described in Ku et al, *Biotech. and Bioeng.*, Vol. XXIII, pp. 79–85 (1981) employs a flat bed hollow-fiber cell culture system, using anisotropic tubing sandwiched between microporous filter plates. The cells attach to a hollow fiber through which a sterile $CO_2$-air mixture is passed. Media flow is directed normal to the plane of the fiber bed. This system, while successful, presents difficulties. Because the system lacks uniform distribution of fibers, dead spaces where insufficient nutrient or oxygen is present can arise, thus leading to tissue necrosis. Moreover, the reactors have limitations in scale in the direction of height. In a system designed by Stanford University, cells are immobilized in the walls of isotropic tubes. Gas is supplied outside the tubes while liquid is supplied in the center. In the Stanford device, large tube wall thicknesses and small porosities represent barriers to adequate gas and liquid diffusion to mammalian cells immobilized in the walls. This limits packing densities and viability of mammalian cells.

SUMMARY OF THE INVENTION

It is an object of the present invention to provide an apparatus and method which alleviates scale and environmental problems present in prior art designs for tissue culture chambers and methods of culturing solid tissue masses.

It is another object of the present invention to provide a simple, economical and effective method and apparatus for the culture of solid tissue masses.

It is a further object of the present invention to provide a method and apparatus for the culture of solid tissue masses wherein tissue necrosis is reduced to a minimum.

It is yet another object of the present invention to provide a method and apparatus for the growth of a solid tissue culture having a radially symmetric cross-section.

These and other objects are achieved by the present invention. Generally, a culture tube is divided into 5 sealed chambers: a culture chamber: a gaseous supply chamber; a liquid supply chamber; a gaseous return chamber and a liquid return chamber. Cell-impermeable hydrophilic tubes extend from the liquid supply chamber, through the culture chamber, to the liquid return chamber. Liquid nutrient flows in the tubes and is transported under differential pressure through the walls thereof to nourish the cells in the culture chamber. Cell-impermeable hydrophobic tubes extend from the gaseous supply chamber, through the culture chamber, to the gaseous return chamber to provide respiratory gases to and remove waste gases from cells in the culture chamber. The apparatus is designed to be radially symmetric and thus provide a uniform tissue culture. Pressure sensors flush-mounted on the walls of the chamber tube, may be provided to monitor chamber conditions and relay this information to a micro-computer which controls each parameter affecting cell proliferation and differentiation. A central tube extends along the longitudinal axis of the culture tube, and is appropriately sectioned and modified to supply liquid nutrient to the liquid supply chamber and remove waste fluids, including soluble product, from the culture chamber.

BRIEF DESCRIPTION OF THE DRAWINGS

FIG. 1 shows a longitudinal cross-section of a preferred embodiment of the present invention.

FIG. 2 shows a cross-section of the embodiment of FIG. 1 taken along line 1—1, looking in the direction of the arrows.

FIG. 3 shows a cross-section of the embodiment of FIG. 1 taken along line 2—2, looking in the direction of the arrows.

FIG. 4 shows a cross-section of the embodiment of FIG. 1 taken along line 3—3, looking in the direction of the arrows.

FIG. 5 shows a cross-section of the embodiment of FIG. 1 taken along line 4—4, looking in the direction of the arrows.

FIG. 8a is a plan view of the macroporous filtration tube used in the preferred embodiment according to present invention.

FIG. 8b is a cross-section of FIG. 8a taken along line 6—6, looking in the direction of the arrows.

FIG. 8c is a cross-section of FIG. 8a taken along line 7—7, looking in the direction of the arrows.

FIG. 8d is a cross-section of FIG. 8a taken along line 8—8, looking in the direction of the arrows.

FIGS. 9a–9f schematically represent various possible configurations of the present invention.

DESCRIPTION OF THE PREFERRED EMBODIMENTS

Figure 6:
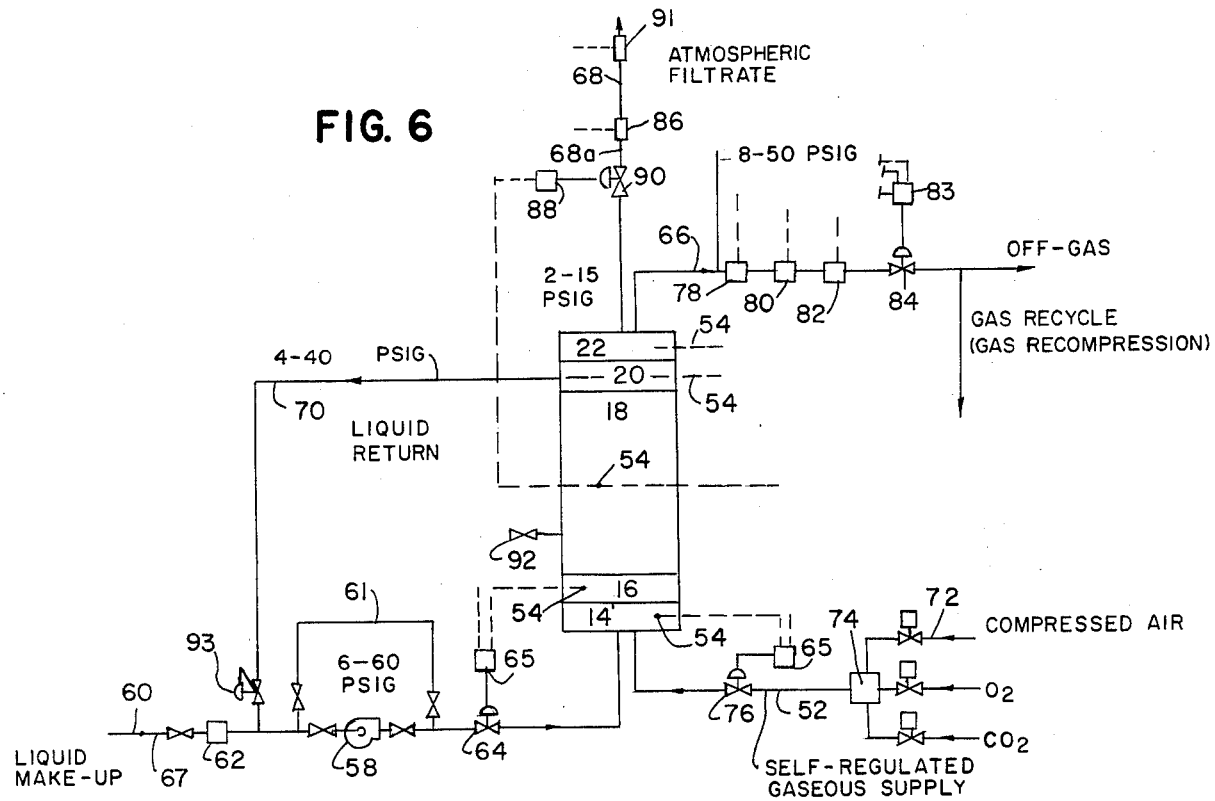
FIG. 6 is a schematic representation of a cocurrent operation scheme employing the present invention.
Figure 7:
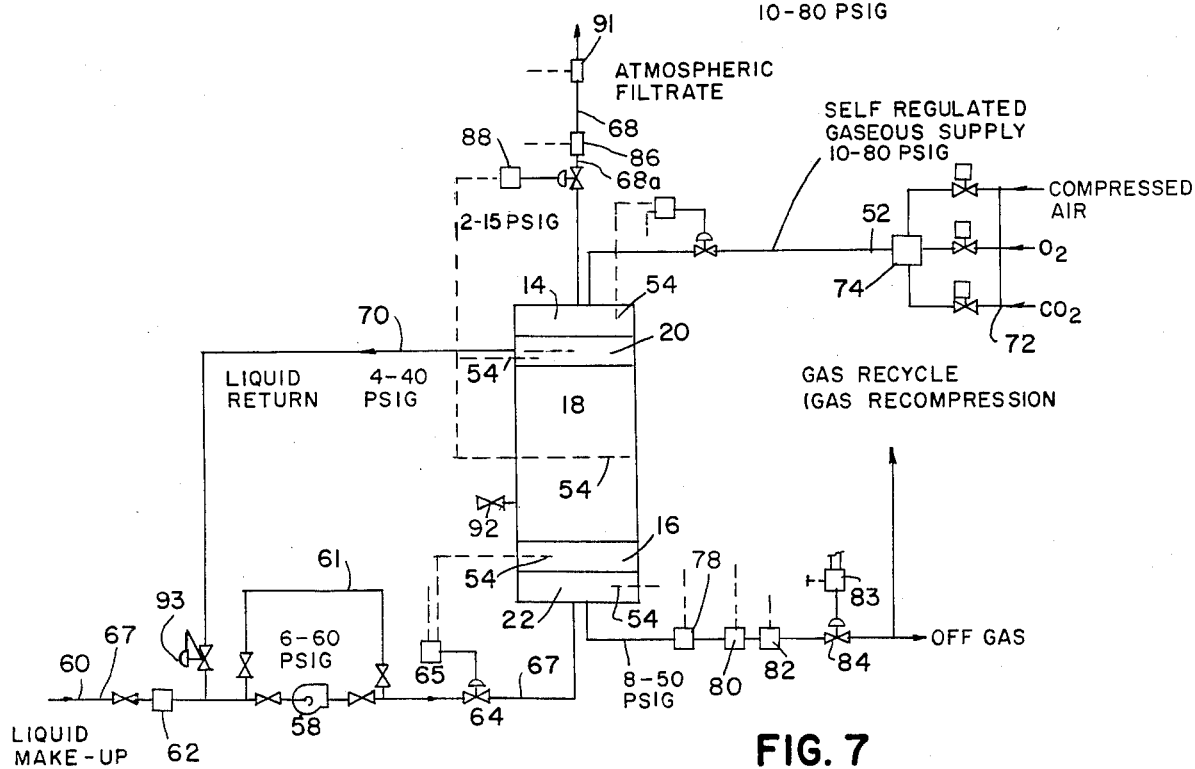
FIG. 7 is a schematic representation of a countercurrent operation scheme employing the present invention.

Referring to FIG. 1, a culture apparatus 10 is formed in a straight culture tube 12. Tube 12 may be formed from upper and lower half shells sealed together along gasket 56 (FIG. 2). The interior of tube 12 is preferably divided into 5 sections: a gaseous supply chamber 14, a liquid supply chamber 16, a culture chamber 18, a liquid return chamber 20 and a gaseous return chamber 22. Each of these chambers are separated from the adjacent chamber by seals 24. The seals 24 are formed in hydrophilic tube bank supports 26, 27 and hydrophobic tube bank supports 28, 29. Typically, seals 24 are formed by introducing an autoclavable and non-cytotoxic sealant, such as Dow MDX Silastic ™ (MDX-4210) into a sealant orifice 30 and allowing the sealant to cure.

Isotropic, microporous (cell-impermeable) hydrophilic tubes 32 (FIG. 2) extend from liquid supply chamber 16 to liquid return chamber 20, parallel to the horizontal axis of tube 12, their ends being open and supported by hydrophilic tube bank supports 26 and 27. Isotropic, microporous (cellimpermeable) hydrophobic tubes 34 (FIG. 2) extend between gaseous supply chamber 14 and gaseous return chamber 22, parallel to the horizontal axis of tube 12, their ends being open and supported by hydrophobic tube bank supports 28 and 29. Hydrophobic tubes 34 also pass through and are supported by hydrophilic tube bank supports 26 and 27. Since seals 24 are added to the tube bank supports 26, 27, 28 and 29 by the addition of sealant, as explained above, after tubes 32 and 34 are set in position, the sealant seals around tubes 32 and 34 and prevents any communication between chambers.

Hydrophilic tubes 32 and hydrophobic tubes 34 are arranged in a radially symmetric fashion, as shown in FIG. 2. Preferably, hydrophilic tubes 32 are at the periphery of the inner wall of tube 12, while hydrophobic tubes 34 are preferentially disposed toward the central horizontal axis of tube 12. Spacing between hydrophobic outside tube walls ranges from 1.5 to 3 mm and preferably from 2-3 mm. Hydrophobic tubes 34 are arranged in a triangular pitch pattern to maximize the normalized cross sectional area to flow.

Macroporous (cell permeable) filter tube 36 extends along the central horizontal axis of tube 12 from one end of culture chamber 18 to the other. Solid-walled tubes 38, 40, integral with macroporous filtration tube 36, each extend from one end of the culture chamber through end walls 42 and 44, respectively along the central horizontal axis. Preferably, tubes 36, 38 and 40 are prepared as a single monolithic unit, referred to as the central tube. This preparation may be accomplished by dipping each end of a macroporous tube into a ceramic or resin liquid which diffuses into and, after curing or annealing, permeates or otherwise seals the pores in the macroporous tube. A plug is inserted in the macroporous tube where solid walled tube 38 jones tube 36. Holes are then drilled in a radially symmetric arrangement in solid-walled tube 38 at positions along solid-walled tube 38 corresponding to liquid supply chamber 16 to form cylindrical diffuser 46.

The inner and outer wall of tube 12 define between them a tubular jacket 48. Within tubular jacket 48 are a plurality of heating channels 50 through which heated water, typically at about 37° C., passes. Preferably, these tubes extend laterally (i.e., horizontally) along the entire length of tubular jacket 48, although the heating channels may be in any configuration and, for example, might only exist in the portion of tubular jacket 48 surrounding culture chamber 18. Also, heating may not be required in some situations or cooling may actually be desired. Nevertheless, in all cases, it is desirable that the temperature be as uniform as possible throughout culture chamber 18. Heating or cooling only culture chamber 18 may result in the ends of culture chamber 18 being cooler or warmer, respectively, than the central portion thereof, causing undesirable convection currents within culture chamber 18 and/or resulting in tissue necrosis from thermal causes.

FIGS. 1-5 itemize the components of the combined hydrophobic and hydrophilic tube banks. Gases 52 enter the gaseous supply chamber 14 and flow into the open ends of the hydrophobic tubes 34. The gases flow through the tubes into the liquid supply chamber 16, oxygenating the liquid in this chamber that flows radially out and around the hydrophobic tube bank. The gases continue flowing through the hydrophobic tubes into the culture chamber 18 and the liquid return chamber 20 and exit the tubes in the gaseous return chamber 22.

The pressures in the culture chamber 18, gaseous supply and return chambers 14, 22, and liquid supply and return chambers 16, 20 are sensed by pressure transducers 54. Pneumatic pressure control valves respond to the signals from the pressure transducers to maintain desired dilution and gas exchange rates in the bioreactor. During normal, steady state operation, the gaseous supply chamber pressure 14, the gaseous return chamber pressure 22, the liquid supply chamber pressure 16, the liquid return chamber pressure 20, and the cell culture chamber pressure 18 are maintained in order of decreasing pressures, respectively. This establishes gas flow through the hydrophobic tubes 34 and liquid flow through hydrophilic tubes 32. The differential pressures between each chamber prevent the cell culture tissue from penetrating the centers of any tubes and also segregates the gases and liquids supplied to the cell culture chamber 18.

As stated above, the liquid in the supply chamber 16 is oxygenated as the liquid flows radially past hydrophobic tube bank 34. Thus, the cell free liquid is oxygenated before entering hydrophilic tubes 32. The hydrophilic tubes 32 carry liquid only and are used to perfuse the cell culture tissue with essential and nonessential amino acids, vitamins and co-factors, supplements, growth and stimulating factors (such as 2ME, hydrocortisone or Poke Weed Mitogen) as well as to maintain the cell culture isotonicity and pH with salts and buffers. Liquid in tubes 32 can move through the tube wall only in one direction. Under a pressure above that of the tissue, bulk fluid flow occurs radially across the tube walls 32 perfusing the cell culture tissue. The radial velocity of the culture liquid into the filtration tube under steady state perfusate conditions 36 increases as liquid approaches the central longitudinal axis of the of culture chamber 18. More than 50% liquid of the liquid delivered to liquid supply chamber 16 does not perfuse through the tube walls 32 and is returned to centrifugal or low shear constant pressure pump 58 (FIG. 6) via the liquid return chamber 20 and liquid return line 70. The liquid supply and return chambers always remain free of animal cells since the tube walls act as a physical barrier to the cells and because the pressure within the hydrophilic and hydrophobic tubes always remains at or above the pressure of the tissue cell culture. The hydrophilic tubes 32 (either rigid glass, zeolites, hydroxyapatite or polymers) preferably have uniform porosity (isotropic) from the inside tube wall to the outside tube wall. The porosity can range from 0.025 to 2 microns depending on the materials of construction and the tube wall thickness. Preferred outside diameters range between 2 and 6 millimeters.

Hydrophobic 34 tubes are used to carry gaseous reactants and products to and from the cell culture chamber 18 providing control of the bioreactor gaseous microenvironment. Concentration gradients are created between the cell culture tissue and the gases carried in the centers of all hydrophobic tubes. Hydrophilic tubes 32 are used to dilute the cell culture tissue for proliferation of cell mass, maintenance of cell mass or production of desired biomolecules.

As stated above, during normal operation the gaseous supply chamber pressure 14 the gaseous return chamber pressure 22 and the culture chamber pressure 18 are maintained in order of decreasing pressures. This establishes gas flow through tubes 34 and prevents the tissue from penetrating the centers of the hydrophobic tubes. The signals from the pressure transducers 54 (4–20 mA) also provide a basis for establishing the integrity of seals 56 (FIG. 5), tubes 32, 34, tube bank supports 26, 27, 28, 29 and sealant 24. Heating channels 50 function to maintain the temperature at 37±0.5 degrees Celcius for animal tissue. Concentration gradients are created between the inside and outside walls of all hydrophobic tubes. The gas supply 52 may consist of an optimum mixture of oxygen, compressed air and carbon dioxide to maximize the production of biomolecules from animal tissues and to stabilize the culture pH between the ranges of about 6.9 and 7.2 pH units.

The gases always flow through tubes 34 at pressures above that of the tissue. Gases first enter tubes 34 through gaseous supply chamber 14, pass through liquid supply chamber 16 in tubes 34 and then diffuse through the tube walls to the tissue culture that forms on the outside of tubes 34. Diffusion of gases through the hydrophobic tube walls occurs in two directions: oxygen, compressed air, and potentially carbon dioxide diffuse from the gas phase into the tissue in culture chamber 18 while ammonia and other volatile substances (including carbon dioxide under high cellular respiration rates) produced by the tissue, which inhibit growth and metabolism, diffuse via concentration gradients from the cell culture tissue into the hydrophobic tubes walls 34. These inhibitory products then diffuse to the center of tubes 34 and are carried to gaseous return chamber 22. Hydrophobic tubes 34 (either rigid glass, zeolites, ceramic or polymers) preferably have uniform porosity (isotropic) from the inside tube wall to the outside tube wall. These materials may be charged modified after tube formation to improve the biocompatibility of the outer tube surface. Pore sizes must be selected to exclude cellular invasion of all hydrophobic tube centers, but large enough to maximize the diffusion rate of gases through the tube walls. Typically, animal cells have diameters of approximately 10 microns and this would exclude tubes with pore sizes greater than 5 microns. The porosity preferably ranges from 0.2 to 2.5 microns depending upon the materials of construction and the tube wall thickness. The maximum range of porosity for hydrophobic tubes lies between about 0.05 to 5 microns. Preferred outside tube diameters range for between hydrophobic tubes 34 between 1 and 3.5 millimeters. Bilaminar tube structures may also be appropriate for hydrophobic tubes 34.

The hydrophilic, isotropic tubes 32 must have well defined radial pressure-flow rate characteristics through the tube walls over a wide range of internal tube pressures. The hydrophilic tube bank 32 must perfuse the liquid into the culture chamber 18 at precisely controlled dilution rates. Therefore, the presure differential across the hydrophilic tube 32 wall must deliver a predictable and controllable flow rate along the entire length of tube 32. The consequence of this requirement is that tubes 32 must be rigid and/or resilient, have uniform porosity across the tube wall, and be able to withstand high pressure differentials across the tube wall without rupturing, or suffering permeability creep or catastrophic failure. Also, the tubes (both hydrophilic 32 and hydrophobic 34) must maintain their spatial configuration to minimize liquid and gaseous mass transfer resistances, and this requires the high degree of rigidity afforded by isotropic tube structure. Moreover, tubes having a uniform porosity (isotropic structure) will act to exclude cells from the center of the tubes. Mammalian cells in the culture chamber 18 must never enter the center of hydrophilic or hydrophobic tubes 32, 34.

The pressure inside the hydrophilic tubes 32 will decrease slightly along the length of each tube because of the pressure drop due to the friction of following liquid inside the tube (liquid that is being forced through the hydrophilic tubes 32 by the centrifugal or constant pressure pump, both of which are designed for low shear) and due to the loss of liquid that is forced radially through the hydrophilic tube walls (the radial flow rate of liquid through the tube wall in any individual hydrophilic tube 32 will be highest just after leaving the liquid supply chamber and slightly lower just before entering the liquid return chamber). Since the liquid flow rates through the tube walls must be as constant along the entire length of the hydrophilic tube 32 as is possible, a high percentage of liquid that enters the hydrophilic tube openings from the liquid supply chamber does not pass through the tube walls but flows through the center of the tube and is returned to the constant pressure pump via the liquid return chamber. The proper tube diameter, tube wall porosity, and tube wall thickness for the hydrophilic tubes 32 maintains uniform radial flow rates through the tube walls along the entire length of the tubes, and insures that the pressure within the tubes remains relatively constant along the tube length.

The filter tube 36 should have an average porosity such that under normal operating conditions (cell sloughage, etc.) the tube does not occlude. Typically, the average porosity is over about 100 microns, preferably between about 100 and 500 microns, and can be as high as 1000 microns. The filter tube 36 could also be constructed with symmetrically arranged holes as large as 1-5 mm distributed around the periphery. The outer diameter of the hydrophobic tubes 34 should be smaller than that of the hydrophilic tubes 32 and should be as small as possible to maximize the area for cell adherence.

To maintain a constant radial flow through hydrophilic tubes walls 32, the length of culture chamber 18 should be selected so that no more than about a 15-20% pressure drop occurs from one end of the hydrophilic tubes to the other. The radial pressure drop (between the periphery of culture chamber 18 and the center of filter tube 36) should be about 0.2-3 psig and preferably about 0.5-1.5 psig. Somewhat higher radial pressure drops of about 2-15 psig., especially 2-10 psig, may also be employed with favorable results. A radial minimum pressure drop of about 0.2 psig is necessary to establish flow between the hydrophilic/hydrophobic tubes 32, 34 and filter tube 36.

The reactor is scalable in the radial direction. An approximate mathematical model for proper scaling are concentric cylinders (up to three or four, typically two) having an inner radius $r_1$ (equal to the outer radius of filter tube 36) and an outer radius $r_2$ (equal to the inner diameter of the cell culture chamber 18). An additional two radii maybe interspaced between the above two. The ratio $r_1/r_2$, as well as the thickness and porosity of filter tube 36, will determine whether the reactor will experience undesirable eddy currents at a given dilution rate and culture chamber pressure. In general, the larger $r_1/r_2$ is, the more unlikely it becomes that complex mixing phenomena will occur. Nevertheless, larger radii (particularly $r_1$) necessitate heavier (i.e., thicker or less porous or both) walls. Since the pressure drop across $r_1$ must be small (less than about 1 psig) to allow chamber pressure control over a range of dilution rates, there is a practical range of ratioes and maximum outside diameters.

The typical pressure ranges of each chamber are listed below:
Culture chamber 18 (2–15 psig);
gaseous supply chamber 14 (10–80 psig);
gaseous return chamber 22 (8–50 psig);
liquid supply chamber 16 (6–60 psig);
liquid return chamber 20 (4–40 psig).

Empirical pressure flow rate studies may be used to determine the exact thickness of the hydrophilic tube wall. Radial flow rates are a function of wall thickness, porosity, internal tube diameter and pressure for a fixed liquid flow rate through the center of the tube. As stated above, the liquid pressure drop inside the hydrophilic tubes 32 (the pressure difference between the liquid supply and liquid return chambers) must not exceed 15 or 20% of the incoming pressure in order to insure that the radial flow rates through the tube wall along the entire tube length are essentially constant. The hydrophobic tube wall thickness must be minimized to ensure that the gas concentration gradients between the inner and outer tube wall surfaces do not exceed values which might inhibit cellular respiration.

Also, there may be some advantage to maintaining gas pressures at or near the bubble point of the hydrophobic tubes 34 (the bubble point is the point at which there is bulk movement of gas through the tube walls, i.e. gas bubbles stream through the surfaces of the tube wall into the culture liquid). Oxygen exchange rates may be enhanced by maintaining the internal tube pressures just below the bubble point of the tube membrane and simultaneously increasing the gas flow rates through the tubes. The isotropic tube structure imparts significant strength per unit wall thickness, and therefore tubes made of isotropic materials can be constructed with significantly thinner wall thickness while still imparting maximum strength for the high internal gas pressures and pressure drops in the tubes which may be required for operating the bioreactor at maximum oxygen absorption efficiency. Also, thinner tube walls will mean that the concentrations of gases in the center of the tube will more closely approximate and gas concentrations on the outer tube wall surface, thus minimizing gaseous concentration gradients.

A certain amount of gas and liquid pressure is needed to maintain the pressure differentials necessary to segregate the chambers of the bioreactor, to exclude cells from the entering the centers of the tubes, and to provide a means of controlling an aseptic environment within the bioreactor. Liquid must not enter centers of hydrophobic gas tubes 34 in either the liquid return or supply chambers, or the culture chamber. This means that the pressures in the gas-carrying hydrophobic tubes 34 must exceed the pressures in the liquid-carrying hydrophilic tubes 32 by a constant value during all periods of operation. The pressure drop experienced as the gases flow inside the hydrophobic tubes 34 (the hydrophobic tube 34 diameters are significantly smaller and hence have larger pressure drops per unit length than the hydrophilic tubes 32) necessitates high internal gas pressures. Again, this means that the tubes must be structurally able to withstand high internal pressure drops as gases flow through the tubes 34.

The tubes, both hydrophilic and hydrophobic, may be constructed from biocompatible materials such as polypropylene, polyvinylidine fluoride, Pyrex TM, polytetrafluoroethylene, zeolites or hydroxyapatite. The hydrophilicity or hydrophobicity of the tubes may be adjusted by charge-modification of the selected polymer or material. For example. polypropylene is normally hydrophobic. When charge-modified, however, polypropylene becomes hydrophilic. Tubes may also be treated chemically to add functional groups, thereby increasing the biocompatibility of the outer tube surface. All tube materials should be sterilizable or at least able to withstand heat sanitization with water at 80° C. The macroporous filtration tube 36 (and of course the central tube) may be suitably composed of a wide variety of materials including a sintered stainless steel and Pyrex TM.

FIG. 6 shows schematically shows one preferred embodiment of a tissue culture system employing the apparatus of the present invention. Nutrient liquid is made up at liquid make up 60. The liquid flows from liquid make up 60, through liquid supply line 67, past mass flow rate indicator 62 and into constant pressure pump 58. A bypass line 61, complete with valves, allows liquid nutrient to bypass around pump 58 when desired. From pump 58, or bypass 61, the liquid nutrient passes through pneumatic pressure control valve, sometimes referred to as modulating valve, 64. The operation of modulating valve 64 is controlled by differential controller 65 under the influence of a micro-computer algorithm which receives signals from pressure transducers 54 in chambers 14, 16, 18, 20 and 22. This algorithm assures that the pressures in the chambers are properly segregated (i.e. liquid does not enter the hydrophobic tubes 34) and that a given (minimum) pressure differential is maintained between the liquid supply chamber 16 and the culture chamber 18.

Liquid nutrient flowing past valve 64 enters liquid supply chamber 16 and flows out through the radial openings 46 into the open ends of hydrophilic tubes 32. Some liquid nutrient passes through the walls of hydrophilic tubes 32 and is dispersed evenly through the tissue culture and later released therefrom as waste into filter tube 36 to form filtrate 68 which exits the apparatus beyond gaseous return chamber 22. The remaining liquid in hydrophilic tubes 32 exits tubes 32 into liquid return chamber 20 and finally into liquid return line 70. Pressure in liquid return line 70 is regulated by back pressure regulator 93 and then liquid is conveyed into liquid supply line 67 where the liquid nutrient is recycled.

Compressed air, oxygen and carbon dioxide pass through gas valve bank 72 into mixer 74 which mixes the gases in proper proportions and passes the mixed gases into gaseous supply line 52. The gases pass through pneumatic pressure control valve 76 which is controlled via a micro-computer algorithm based on the inputs obtained from pressure transducers 54 in gaseous supply chamber 14, culture chamber 18 and gaseous return chamber 22. The algorithm assures that the chambers are properly segregated (i.e., no liquid enters hydrophobic tubes 34) and the proper gas pressure differential is maintained between gaseous supply chamber 14 and gaseous return chamber 22 over all ranges of gas flow rates.

After the mixed gases pass through pressure control valve 76, they pass into gaseous supply chamber 14, whereupon they enter hydrophobic tubes 34. Once in culture chamber 18, the mixed gases diffuse through the walls of hydrophobic tubes 34 in the cell culture while waste gases from the cells, including $CO_2$, diffuse into the hydrophobic tubes 34. The waste gases and unspent mixed gases then pass through liquid return chamber 20 prior to emptying into gaseous return chamber 22 and then gaseous return line 66. From gaseous return line 66, the returning gases are analyzed using a gas flow meter 78, $CO_2$ infrared analyzer 80 and an $O_2$ analyzer 82. The information obtained from this analysis is processed by an algorithm 83 and used to regulate the exit gas flow control valve 84. The waste gases are then removed and the remaining gases are recompressed and may be recycled.

The atmospheric filtrate 68, containing waste liquid and cellular debris, is conveyed via filtrate line 68a and analyzed for reduced NADH by a fluorescent spectrophotometer 86 and pH sensor 91. The information obtained by these analyses is used by a micro-computer (not shown) to determine the correct gas ratioes and liquid feed rates. This information may also be used to adjust gas flow rates. Mini-computer algorithm 88 controls the back-pressure presented by culture chamber 18 upon filter tube 36 via modulating control valve 90. The culture chamber pressure may be controlled by valve 90 up to 15 psig. This creates a hyperbaric environment and thereby increases the oxygen carrying capacity of the culture chamber liquid.

The above described configuration is called the cocurrent configuration, since both gas and liquid flow occur in the same direction. Alternative cocurrent configurations are shown in FIGS. 9a–c. In the cocurrent configurations of FIGS. 6 and 9a a significant advantage is that, since the oxygen-rich mixed gases are in hydrophobic tubes 34 passing through liquid supply chamber 16, the liquid in liquid supply chamber is pre-oxygenated prior to entering hydrophilic tubes 32.

FIGS. 7 and 9d–f show countercurrent embodiments of the present invention. No pre-oxygenation occurs in these embodiments. Thus, cells at the end of chamber 18 where gas exits could, under some circumstances, experience an excess of $CO_2$ or a deficiency of $O_2$. Nevertheless, on a small scale, countercurrent embodiments should be useful. Also, $O_2$ deficiency could be prevented in the arrangement of FIG. 7 by enriching the incoming gases with respect to oxygen so that the exiting liquid can be reoxidized prior to recycling liquid to supply chamber 16. Or, the gaseous supply line 52 could be enriched with respect to oxygen and passed through liquid supply line 22 after make-up to pre-oxygenate the incoming liquid.

Solid tissue masses may be trypsinized at the end of a production run and cells allowed to pass through the macroporous filtration tube until the chamber is empty. Alternatively the reactor can be opened and the tissue mass removed externally. After cells have been removed and/or the chamber reassembled, clean steam may be supplied to the gaseous supply chamber and allowed to flow through the tubes. Likewise, clean steam may also be allowed to pass through the liquid tubes via the liquid supply (cylindrical diffuser) and liquid return chambers. Pressures in the tubes (typically saturated steam at about 15 psi) force steam into the culture chamber 18 and into the macroporous filtration tube 36 (condensate exits through the outlet). Vent value 92 may also be used to purge or add steam to culture chamber 18. This sterilization regime assures that all liquid and gas contact surfaces (as well as the culture chamber) are appropriately sterilized.

The reactor is inoculated after sterilization or heat sanitization of all internal contact surfaces. Cells can be introduced into the culture chamber through the filtration tube which runs along the center axis of the reactor. The modulating valve on the culture chamber filtrate 90, 88 is opened fully and isolating valves around pump 58 closed. Cells are forced under pressure into the tube and through the wall of the macroporous tube 36. Cells are excluded from entering the liquid supply/return and gaseous supply/return chambers during introduction into the culture chamber by virtue of the fact that the central tube walls are constructed of non-permeable materials except in culture chamber 18, which portion 36 is porous tube wall greater than 100 microns. Pressure build-up in the culture chamber 18 is prevented from occurring during inoculation of the bioreactor by venting through the hydrophilic tube bank 32 or perferably through vent valve 92. Inoculation may take place in a vertical position, with the cells being introduced from below, so as to prevent unequal distribution of cells which might otherwise result from gravitational settling. Alternatively cells may be introduced into culture chamber 18 through vent valve 92. After the cells have been inoculated into culture chamber 18, valve 90 should be fully closed until respiratory functioning occurs, as indicated by the various above-mentioned monitors.

After inoculation of the culture chamber 18 with cells, a given (minimum) pressure differential is maintained between the gaseous supply chamber 14 and the culture chamber 18. Also a minimum set point for bleeding off gas (83,84) is maintained. This algorithm assures all chambers are segregated i.e., liquid does not enter the gas tubes and that a sufficient $O_2$/$CO_2$/compressed air mixture is supplied for initiating growth of the tissue mass. Tissue mass accumulation is determined by off-gas analysis. When $CO_2$ concentration exceeds a set point, or when the $O_2$ concentration becomes sufficiently low, more gas is allowed to flow through the tubes by slowly ramping modulating valve 84, 83 on gaseous return line 66. The modulating valve 76, 65 controlling the pressure difference between the gaseous supply and culture chamber will also ramp open to maintain the necessary pressure differentials that assure complete segregation between all chambers.

During initial culturing, the gravitational settling of cells should be avoided. This may be accomplished by slow, reciprocating 180° planetary rotation of the entire assembly. Alternatively, the culture system may be structured to rotate in a planetary fashion 360°. To achieve this end, the macroporous tube 38, 36, 40 may be connected near ends 42 and 44 to the respective liquid supply and return lines by rotatable seals. Similarly, the gas and liquid supply and return chamber may be connected to the supply and return lines by rotating seals. All electrical lines connected at one end and to a stationary object and at the other to the rotating culture system may be connected by a rotatable contact. Thus, continuous, 360° planetary rotation may be accomplished without twisting wires or tubing connected to the apparatus. A similar technology to prevent twisting is described in U.S. Pat. No. 4,051,025, issued Sept. 27, 1977, to Ito, incorporated by reference herein.

Figure 10:
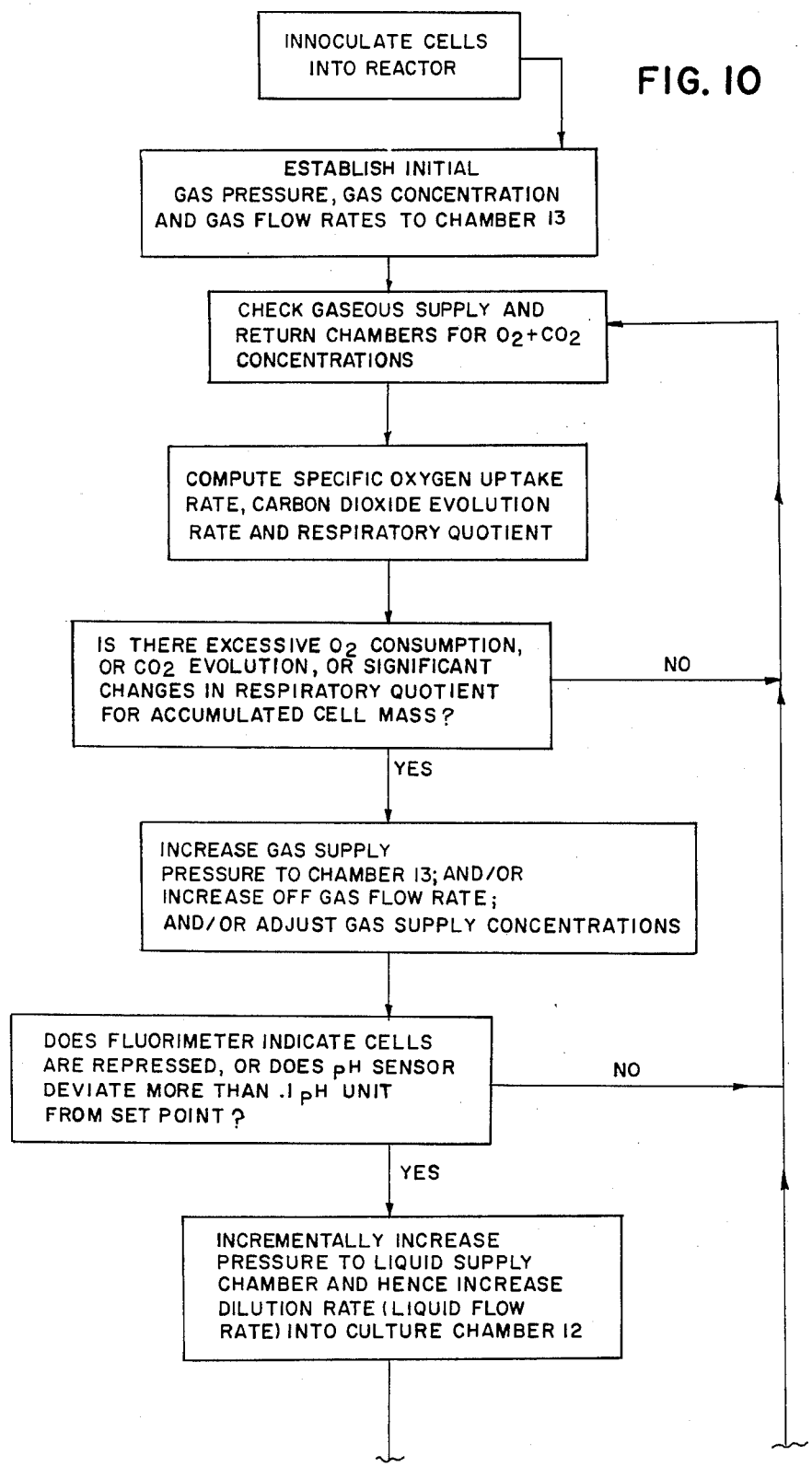
FIG. 10 is a flow chart defining a microcomputer algorithm for controlling gas pressures and flow rates, liquid pressures and dilution rates during operation of the present invention.
Figure 10:
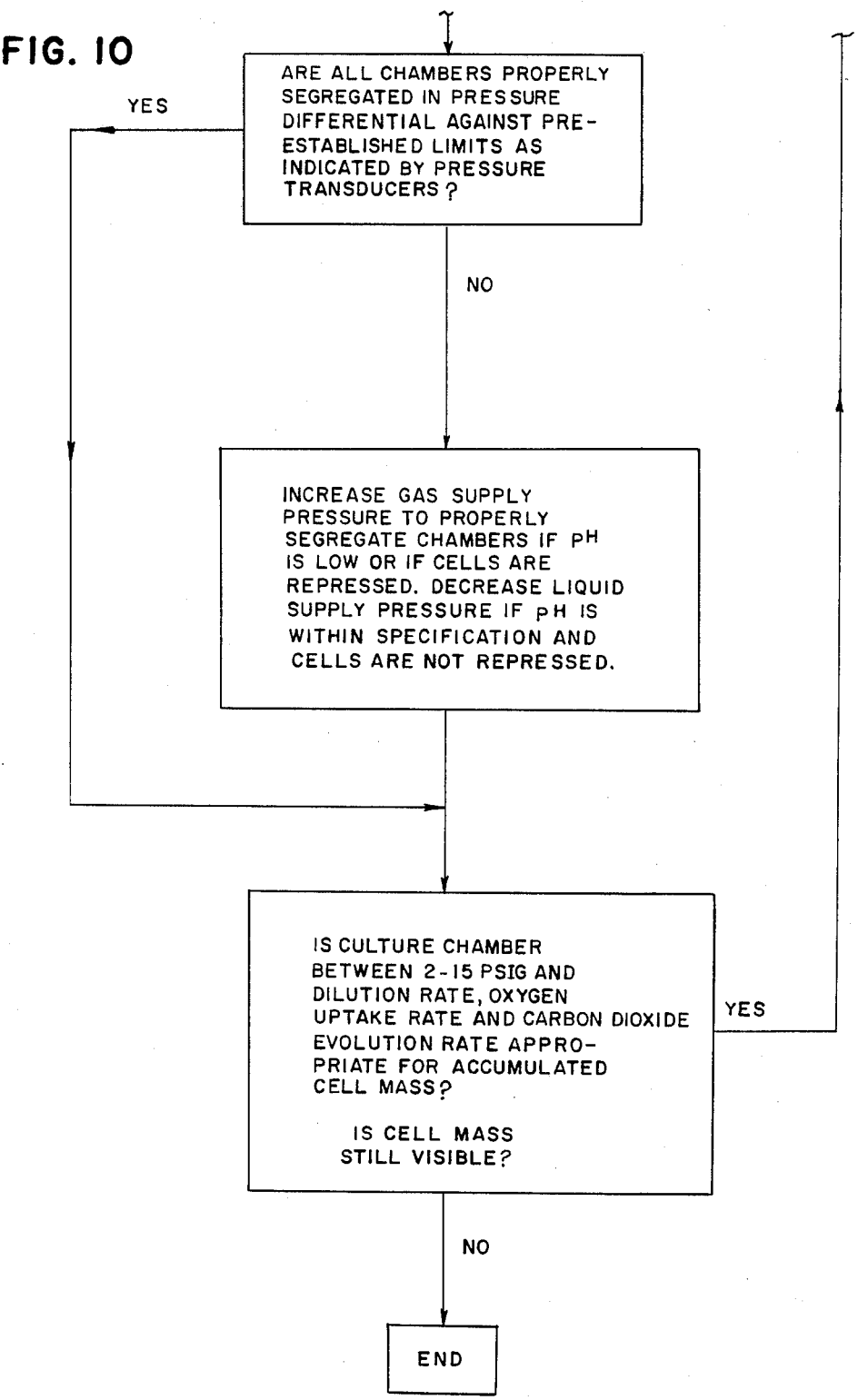

As noted above, the liquid and gas pressures and flow rate in each chamber are ultimately controlled by a series of algorithm subroutines combining to form one algorithm. Because this algorithm can vary depending on the exact construction of the embodiment used, this specification does not describe the algorithm used. Instead, FIG. 10 shows a flow chart of general application used for controlling liquid and gaseous pressure and flow rates from which, for any given circumstance, a suitable algorithm may be developed by the simple exercise of skill ordinary in the art.

The present invention allows great degree of control over each parameter which might affect cell proliferation or excretion of cellular product. Thus, the present invention is highly flexible and may be adapted to culture a variety of solid tissue cells and tailor conditions to favor the production of a great number of products. A desirable protocol would be to empirically find the best normal proliferative conditions (parameters) for the type of cell being cultured and then vary each parameter, individually at first, noting the effects of this variance upon cell differentiation and production of the desired product. Ultimately, using this approach, one skilled in the art can arrive at the optimal conditions for the production of a cellular product.

Figure 11:
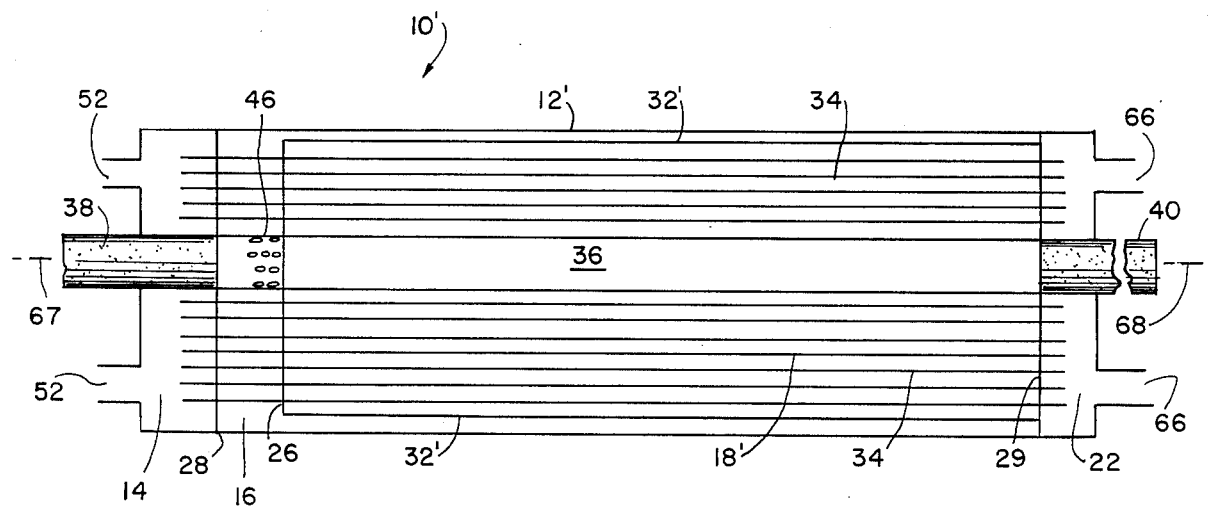
FIG. 11 schematically shows an alternative embodiment of the present invention.

One possible modification 10' of the present invention would be to use a single, large diameter hydrophilic tube 32' and similarly radially arranged hydrophobic tubes 34 (FIG. 11). This embodiment would eliminate the necessity for a liquid return chamber and several seals. Liquid nutrient enters the space between hydrophilic tube 32' and tube 12' from liquid supply chamber 16 and enters into hydrophilic tube 32' within culture chamber 12'.

It is to be understood that the present invention is not limited to the embodiments disclosed which are illustratively offered and that modifications may be made without departing from the invention.

What is claimed is:

1. A culture apparatus for tissue culture growth, comprising:
   a straight culture tube;
   a plurality of gas-permeable and cell-impermeable essentially rigid hydrophobic tubes within said culture tube extending parallel to a central longitudinal axis of said culture tube and arranged in a radially symmetric pattern;
   a plurality of essentially rigid hydrophilic, cell-impermeable tubes within said culture tube extending parallel to said horizontal axis and arranged in a radially symmetric pattern;
   said culture tube being longitudinally divided into five distinct chambers as follows:
   a culture chamber within said culture tube;
   a liquid supply chamber within said culture tube;
   a gas supply chamber within said culture tube;
   a liquid return chamber within said culture tube, said liquid return chamber and said liquid supply chamber being positioned so that said culture chamber is positioned therebetween;
   a gas return chamber within said culture tube, said gas return chamber and said gas supply chamber being positioned so that said culture chamber is positioned therebetween;
   a plurality of radially extending seals within said culture tube, said seals defining passages therein for said hydrophilic and hydrophobic tubes, each of said seals separating one of said chambers from an adjoining chamber;
   each of said hydrophobic tubes extending from the gas supply chamber, through said culture chamber, to the gas return chamber;
   each of said hydrophilic tubes extending from the liquid supply chamber, through said culture chamber, to the liquid return chamber;
   a conduit for conveying a tissue culture filtrate away from said culture tube, said conduit being positioned outside said culture tube;
   a central tube within and cocentric with said culture tube and extending from one end of said culture tube to said conduit;
   said central tube having a first solid-walled portion extending from an end of said culture tube closest said liquid supply chamber to said liquid supply chamber, said first solid-walled portion including means defining radially arranged holes in said solid wall for diffusing liquid within said central tube into said liquid supply chamber; a macroporous section extending from one end of said culture chamber to the other, a plug sealing the interior of said central tube between said holes and an end of said liquid supply chamber closest said culture chamber, and a second solid-walled portion extending between said culture chamber and said conduit.

2. The culture apparatus of claim 1, wherein the spacing between the peripheral surfaces of said hydrophobic tube walls is about 1.5-3 mm.

3. The culture apparatus of claim 2, wherein the spacing between the peripheral surfaces of said hydrophobic tube walls is about 2-3 mm.

4. The culture apparatus of claim 2 wherein the porosity of said hydrophobic tubes is about 0.05-5 microns.

5. The culture apparatus of claim 4 wherein the porosity of said hydrophobic tubes is about 0.2-2.5 microns.

6. The culture apparatus of claim 4 wherein said hydrophilic tubes have a porosity of about 0.025-2 microns.

7. The culture apparatus of claim 6 wherein said macroporous section of said central tube has a porosity of about 100-1000 microns.

8. The culture apparatus of claim 7 wherein said macroporous section has a porosity of about about 100-500 microns.

9. The culture apparatus of claim 6 wherein said macroporous section of said central tube defines symmetrically arranged holes evenly distributed about the periphery thereof, said holes ranging about 1-5 mm in diameter.

10. The culture apparatus of claim 6 wherein said hydrophobic tubes and said hydrophilic tubes are made of a material selected from the from the group consisting of rigid ceramics and rigid polymers.

11. The culture apparatus of claim 10 wherein said hydrophilic tubes and said hydrophobic tubes are made of materials selected from the group consisting of heatresistant glass, zeolites, polypropylene, polyvinylidine fluoride and hydroxyapatite.

12. The culture apparatus of claim 11 wherein the materials used for said hydrophilic tubes are charge-modified.

13. The culture apparatus of claim 6, further comprising:
   means for maintaining the pressure within said culture chamber at about 2-15 psig;
   the pressure within said gas supply chamber at about 10-80 psig;
   the pressure within said gas return chamber at about 8-50 psig;
   the pressure within said liquid supply chamber at about 6-60 psig;
   the pressure within said liquid return chamber at about 4-40 psig;
   the pressure within the liquid return chamber at a value less than about 20% below the pressure within the liquid supply chamber;
   the radial pressure drop between 0.2-15 psig;
   wherein said means for maintaining maintains said gas supply chamber, said gas return chamber, said liquid supply chamber, said liquid return chamber and said culture chamber in order of decreasing pressure; and
   wherein said means for maintaining maintains a pressure differential between said gas supply chamber and said return chamber sufficient with respect to the pressure differential between said liquid supply chamber and said liquid return chamber so that a higher pressure is maintained in said hydrophobic tubes than in said hydrophilic tubes so as to prevent the entry of liquid from said hydrophilic tubes into said hydrophobic tubes.

14. The culture apparatus of claim 13, said pressure maintaining means comprising means for monitoring the pressures within each of said chambers and sending signals indicating the pressure within each of said chambers to a microcomputer, said microcomputer comprising means for controlling said pressure maintaining means based on said pressure indicating signals.

15. The culture apparatus of claim 1 wherein said hydrophilic and hydrophobic tubes are isotropic.

16. A method of tissue culture comprising the steps of:
   providing a cell culture apparatus including:
   a straight culture tube;
   a plurality of gas-permeable and cell-impermeable essentially rigid hydrophobic tubes within said culture tube extending parallel to a central longitudinal axis of said culture tube and arranged in a radially symmetric pattern;
   a plurality of essentially rigid hydrophilic, cell-impermeable tubes within said culture tube extending parallel to said horizontal axis and arranged in a radially symmetric pattern;
   said culture tube being longitudinally divided into five distinct chambers as follows:
   a culture chamber within said culture tube;
   a liquid supply chamber within said culture tube;
   a gas supply chamber within said culture tube;
   a liquid return chamber within said culture tube, said liquid return chamber and said liquid supply chamber being positioned so that said culture chamber is positioned therebetween;
   a gas return chamber within said culture tube, said gas return chamber and said gas supply chamber being positioned so that said culture chamber is positioned therebetween;
   a plurality of radially extending seals within said culture tube, said seals defining passages therein for said hydrophilic and hydrophobic tubes, each of said seals separating one of said chambers from an adjoining chamber;
   each of said hydrophobic tubes extending from the gas supply chamber, through said culture chamber, to the gas return chamber;
   each of said hydrophilic tubes extendng from the liquid supply chamber, through said culture chamber, to the liquid return chamber;
   a conduit for conveying a tissue culture filtrate away from said culture tube, said conduit being positioned outside said culture tube;
   a central tube within and cocentric with said culture tube and extending from one end of said culture tube to said conduit;
   said central tube having a first solid-walled portion extending from an end of said culture tube closest said liquid supply chamber to said liquid supply chamber, said first solid-walled portion including means defining radially arranged holes in said solid wall for diffusing liquid within said central tube into said liquid supply chamber; a macroporous section extending from one end of said culture chamber to the other, a plug sealing the interior of said central tube between said holes and an end of said liquid supply chamber closest said culture chamber, and a second solid-walled portion extending between said culture chamber and said conduit;
   introducing an innoculum comprising tissue cells into said culture chamber;
   introducing a nutrient liquid into said liquid supply chamber, whereby said nutrient liquid enters open ends of said hydrophilic tubes, a portion of said nutrient liquid within said hydrophilic tubes passes out through the walls thereof, and the remaining portion of said nutrient fluid exits from said hydrophilic tubes into said liquid return chamber;
   maintaining the pressure within said culture chamber at about 2-15 psig;
   maintaining the pressure within said gas supply chamber at about 10-80 psig;
   maintaining the pressure within said gas return chamber at about 8-50 psig;
   maintaining the pressure within said liquid supply chamber at about 6-60 psig;
   maintaining the pressure within said liquid return chamber at about 4-40 psig;
   maintaining the pressure within the liquid return chamber at a value no less than 20% below the pressure within the liquid supply chamber;
   maintaining the radial pressure drop between about 0.2-15 psig;
   maintaining said gas supply chamber, said gas return chamber, said liquid supply chamber, said liquid return chamber and said culture chamber in order of decreasing pressure; and
   maintaining the pressure differential between said gas supply chamber and said return chamber sufficient with respect to the pressure differential between said liquid supply chamber and said liquid return chamber so that a higher pressure is maintained in said hydrophobic tubes than in said hydrophilic tubes so as to prevent the entry of liquid from said hydrophilic tubes into said hydrophobic tubes;

whereby liquid containing wastes and cellular product from said tissue cells passes into said macroporous section and then into said second solid-walled portion;

introducing a mixture of raw gases comprising $CO_2$, $O_2$ and air into said gas supply chamber, whereby said mixture of gases enters the hydrophobic tubes then passes out through said hydrophobic tubes, and the remaining portion of said mixture of gases exits said hydrophobic tubes and enters said gas return chamber, and gaseous wastes diffuse through the walls of said hydrophobic tubes and exit said hydrophobic tubes to enter into said gas return chamber;

monitoring the $O_2$ and $CO_2$ concentration of said wastecontaining mixture of gases received in said gas return chamber;

monitoring the concentration of reduced NADH and pH present in waste-containing liquid received in said macroporous section;

monitoring the pressure within each of said chambers; and controlling, based upon said monitored $O_2$, $CO_2$ and reduced NADH and pH concentrations and said monitored pressures, the pressure within each of said chambers, and the flow rates of said liquid nutrient and said mixture of raw gases.

17. The method of claim 16 and further comprising recycling said nutrient liquid to said liquid supply chamber from said liquid return chamber.

18. A culture apparatus for tissue culture growth, comprising:

a straight culture tube;

a plurality of gas-permeable and cell-impermeable essentially rigid hydrophobic tubes within said culture tube extending parallel to a central longitudinal axis of said culture tube and arranged in a radially symmetric pattern;

an essentially rigid hydrophilic, cell-impermeable tube within said culture tube, extending parallel to and cocentric with said horizontal axis and surrounding said hydrophobic tubes;

said culture tube being longitudinally divided into four distinct chambers as follows:

a culture chamber within said culture tube;

a liquid supply chamber within said culture tube;

a gas supply chamber within said culture tube;

a gas return chamber within said culture tube; said gas return chamber and said gas supply chamber being positioned so that said culture chamber is positioned therebetween;

a plurality of radially extending seals within said culture tube, said seals defining passages therein for said hydrophilic and hydrophobic tubes, each of said seals separating one of said chambers from an adjoining chamber;

each of said hydrophobic tubes extendng from the gas supply chamber, through said culture chamber, to the gas return chamber;

said hydrophilic tube extending from the liquid supply chamber through at least said culture chamber; and a conduit for conveying a tissue culture filtrate away from said culture tube, said conduit being positioned outside said culture tube;

a central tube within and cocentric with said culture tube and extending from one end of said culture tube to said conduit;

said central tube having a first solid-walled portion extending from an end of said culture tube closest said liquid supply chamber to said liquid supply chamber, said first solid-walled portion including means defining radially arranged holes in said solid wall for diffusing liquid within said central tube into said liquid supply chamber; a macroporous section extending from one end of said culture chamber to the other, a plug sealing the interior of said central tube between said holes and the end of said liquid supply chamber closest said culture chamber, and a second solid-walled portion extending between said culture chamber and said conduit.

* * * * *